United States Patent
Wakui

(10) Patent No.: US 11,037,292 B2
(45) Date of Patent: Jun. 15, 2021

(54) CELL IMAGE EVALUATION DEVICE AND CELL IMAGE EVALUATION CONTROL PROGRAM

(71) Applicant: FUJIFILM Corporation, Tokyo (JP)

(72) Inventor: Takashi Wakui, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 58 days.

(21) Appl. No.: 16/431,229

(22) Filed: Jun. 4, 2019

(65) Prior Publication Data

US 2019/0287244 A1 Sep. 19, 2019

Related U.S. Application Data

(63) Continuation of application No. PCT/JP2017/042472, filed on Nov. 28, 2017.

(30) Foreign Application Priority Data

Dec. 6, 2016 (JP) .............................. JP2016-236441

(51) Int. Cl.
*G06K 9/00* (2006.01)
*G06T 7/00* (2017.01)
(Continued)

(52) U.S. Cl.
CPC .............. *G06T 7/0012* (2013.01); *C12M 1/34* (2013.01); *G01N 15/1475* (2013.01);
(Continued)

(58) Field of Classification Search
CPC ......... G06T 7/0012; G06T 2207/30024; G06T 7/90; G06T 2207/10056;
(Continued)

(56) References Cited

U.S. PATENT DOCUMENTS 7,160,681 B2 * 1/2007 Gelfand ............... C12Q 1/6886
435/6.14
10,755,078 B2 * 8/2020 Rubin ................. G01N 33/5058
(Continued)

FOREIGN PATENT DOCUMENTS

JP 2008-276290 A 11/2008
JP 2011-229409 A 11/2011
(Continued)

OTHER PUBLICATIONS

Japanese Office Action, dated May 26, 2020, for corresponding Japanese Application No. 2018-554928, with an English translation.
(Continued)

*Primary Examiner* — Sheela C Chawan
(74) *Attorney, Agent, or Firm* — Birch, Stewart, Kolasch & Birch, LLP

(57) ABSTRACT

An evaluator 21 that evaluates states of cells included in each region of interest of a cell image, and a predictor 22 that performs, in advance, machine learning of a relationship between evaluation results for a specific region of interest within a first cell image obtained by imaging cells before a staining process and regions around the specific region of interest and staining states of cells of the specific region of interest within a second cell image obtained by imaging the same imaging targets as the cells of the first cell image after the staining process are provided. The predictor 22 predicts staining states of cells of a specific region of interest based on evaluation results for the specific region of interest and regions around the specific region of interest among the evaluation results for the third cell image of the cells before the staining process.

20 Claims, 11 Drawing Sheets

(51) Int. Cl.
 G06T 7/90 (2017.01)
 G01N 15/14 (2006.01)
 C12M 1/34 (2006.01)
 G01N 21/27 (2006.01)
 G01N 33/48 (2006.01)
 G01N 33/483 (2006.01)

(52) U.S. Cl.
 CPC ............ G01N 21/27 (2013.01); G01N 33/48 (2013.01); G01N 33/483 (2013.01); G06K 9/00 (2013.01); G06T 7/90 (2017.01); G06T 2207/10056 (2013.01); G06T 2207/20081 (2013.01); G06T 2207/30004 (2013.01)

(58) Field of Classification Search
 CPC ........... G06T 2207/20081; G06T 2207/30004; C12M 1/34; C12M 41/36; G01N 21/27; G01N 33/48; G01N 33/483; G01N 15/1475; G06K 9/0014; G06K 9/00; G06K 9/00147; G16H 30/40; G16H 50/20
 USPC ....... 382/100, 128, 129, 130, 131, 132, 133, 382/134, 155, 156, 157, 158, 159, 203, 382/224, 225, 226, 227, 168, 169, 190, 382/237
 See application file for complete search history.

(56) References Cited

U.S. PATENT DOCUMENTS

| | | | |
|---|---|---|---|
| 2003/0039998 A1* | 2/2003 | Gelfand | G01N 33/57496 435/6.13 |
| 2010/0002929 A1 | 1/2010 | Sammak et al. | |
| 2012/0052524 A1* | 3/2012 | Kinooka | G01N 33/5029 435/29 |
| 2013/0109051 A1 | 5/2013 | Li et al. | |
| 2014/0270457 A1 | 9/2014 | Bhargava | |
| 2015/0219543 A1* | 8/2015 | Yamauchi | G01N 15/00 356/335 |
| 2016/0035093 A1 | 2/2016 | Kateb et al. | |
| 2016/0078275 A1 | 3/2016 | Wang et al. | |
| 2016/0163049 A1 | 6/2016 | Matsubara et al. | |
| 2016/0253466 A1 | 9/2016 | Agaian et al. | |
| 2017/0011512 A1 | 1/2017 | Matsubara | |
| 2017/0081628 A1 | 3/2017 | Matsubara | |
| 2018/0239949 A1* | 8/2018 | Chander | G06N 20/20 |

FOREIGN PATENT DOCUMENTS

| | | | |
|---|---|---|---|
| JP | 2011229409 A * | 11/2011 | ............ C12M 41/14 |
| JP | 2016-509845 A | 4/2016 | |
| WO | WO 2011/162213 A1 | 12/2011 | |
| WO | WO 2015/025508 A1 | 2/2015 | |
| WO | WO 2015/146064 A1 | 10/2015 | |
| WO | WO 2015/182382 A1 | 12/2015 | |

OTHER PUBLICATIONS

Extended European Search Report, dated Nov. 22, 2019, for European Application No. 17879101.8.
Korean Office Action dated Jun. 5, 2020, for corresponding Korean Patent Application No. 10-2019-7015612, with English translation.
International Preliminary Report on Patentability and Written Opinion of the International Searching Authority (forms PCT/IB/373, PCT/ISA/237 and PCT/IB/326), dated Jun. 20, 2019, for corresponding International Application No. PCT/JP/2017/042472, with a Written Opinion translation.
International Search Report (form PCT/ISA/210), dated Feb. 20, 2018, for corresponding International Application No. PCT/JP2017/042472, with an English translation.
Wang et al., "Novel Cell Segmentation and Online SVM for Cell Cycle Phase Identification in Automated Microscopy," Bioinformatics, vol. 24, No. 1, 2008 (Advance Access Publication Nov. 7, 2007), pp. 94-101.
Adamzyk et al., "Different Culture Media Affect Proliferation, Surface Epitope Expression, and Differentiation of Ovine MSC", Stem Cells International, vol. 2013, Article ID 387324, pp. 1-13 (15 pages total).
Japanese Office Action dated Sep. 1, 2020 for corresponding Application No. 2018-554928 with an English translation.
Lundqvist et al., "Optimisation of culture conditions for differentiation of C17.2 neural stem cells to be used for in vitro toxicity tests", Toxicology Vitro, vol. 27, 2013 (Available online Apr. 27, 2012), pp. 1565-1569.
Ojala et al., "Culture Conditions Affect Cardiac Differentiation Potential of Human Pluripotent Stem Cells", PLOS ONE, vol. 7, Issue 10, Oct. 2012, pp. 1-13 (14 pages total).
Korean Notice of Final Rejection for corresponding Korean Application No. 10-2019-7015612, dated Dec. 14, 2020, with an English translation.

* cited by examiner

FIG. 6

I BEFORE STAINING PROCESS

| | | | | | | | |
|---|---|---|---|---|---|---|---|
| 2 | 2 | 2 | 2 | 2 | 2 | 2 | 1 |
| 2 | 2 | 2 | 2 | 2 | 2 | 2 | 1 |
| 1 | 1 | 2 | 1 | 1 | 1 | 1 | 1 |
| 1 | 1 | 2 | 3 | 3 | 3 | 3 | 3 |
| 1 | 1 | 1 | 3 | 5 | 3 | 4 | 4 |
| 1 | 1 | 1 | 5 | 5 | 4 | 4 | 4 |
| 1 | 1 | 4 | 4 | 4 | 4 | 4 | 4 |
| 1 | 1 | 4 | 4 | 4 | 4 | 4 | 4 |
| 1 | 1 | 1 | 4 | 4 | 4 | 4 | 4 |
| 1 | 1 | 1 | 1 | 1 | 1 | 1 | 1 |
| 1 | 1 | 1 | 1 | 1 | 1 | 1 | 1 |

ER21, ER11, ER31, R

↓

II AFTER STAINING PROCESS

| | | | | | | | |
|---|---|---|---|---|---|---|---|
| 2 | 2 | 2 | 2 | 2 | 2 | 2 | 2 |
| 2 | 2 | 2 | 2 | 2 | 2 | 2 | 2 |
| 2 | 2 | 2 | 2 | 2 | 2 | 2 | 2 |
| 2 | 2 | 2 | 2 | 2 | 2 | 2 | 2 |
| 2 | 2 | 2 | 2 | 2 | 2 | 2 | 2 |
| 1 | 1 | 2 | 5 | 5 | 4 | 4 | 4 |
| 1 | 1 | 2 | 5 | 5 | 5 | 4 | 4 |
| 1 | 1 | 3 | 3 | 5 | 4 | 4 | 5 |
| 1 | 4 | 5 | 5 | 5 | 4 | 4 | 5 |
| 1 | 4 | 4 | 4 | 4 | 4 | 4 | 4 |
| 1 | 1 | 4 | 4 | 4 | 4 | 1 | 1 |
| 1 | 1 | 1 | 4 | 4 | 1 | 1 | 1 |

ER22, ER12, ER32

| LEARNING FEATURE VALUES | | LEARNING CLASS |
|---|---|---|
| 111111144 | ⇒ | 4 |
| 122122222 | | 2 |
| 312312311 | | 2 |
| ......... | | ... |
| ......... | | ... |
| ......... | | ... |

CELL IMAGE EVALUATION DEVICE AND CELL IMAGE EVALUATION CONTROL PROGRAM

CROSS-REFERENCE TO RELATED APPLICATIONS

This application is a Continuation of PCT International Application No. PCT/JP2017/042472 filed on Nov. 28, 2017, which claims priority under 35 U.S.C § 119(a) to Patent Application No. 2016-236441 filed in Japan on Dec. 6, 2016, all of which are hereby expressly incorporated by reference into the present application.

BACKGROUND OF THE INVENTION

1. Field of the Invention

The present invention relates to cell image evaluation device and program which predict staining states of cells included in a cell image based on evaluation results for the cell image.

2. Description of the Related Art

Pluripotent stem cells such as embryonic stem (ES) cells and induced pluripotent stem (iPS) cells have ability to differentiate into cells of various tissues, and have received attention as being applicable to regenerative medicine, drug development, and elucidation of diseases.

Meanwhile, a method of determining a differentiated state of the cells by imaging the pluripotent stem cells such as the ES cells and the iPS cells or differentiated and induced cells by using a microscope and capturing features of an image thereof has been suggested in the related art.

For example, JP2011-229409A suggests a method of extracting a region occupied by ES cells and a region occupied by feeder cells from an image obtained by imaging the ES cells and the feeder cells, calculating feature values indicating morphological features of the feeder cells present in the region occupied by the ES cells, and evaluating states of the ES cells by using a fuzzy neural network based on a correspondence between the feature values and states of the ES cells.

SUMMARY OF THE INVENTION

Here, as a method of evaluating an undifferentiated state and differentiated state of the pluripotent stem cells, there is a staining process using a staining marker such as alkaline phosphatase. Since the undifferentiated cells are stained and the differentiated cells are not stained depending on the kind of alkaline phosphatase, it is possible to check whether or no cells as culturing targets are maintained in the undifferentiated state.

However, since the staining process using the staining marker is a destruction process, the cells on which the staining process is performed once are not able to be continuously cultured again since then.

Meanwhile, as a method of evaluating whether the cultured cells are in the undifferentiated state or the differentiated state, there is a method of analyzing the feature values of the cell image obtained by imaging the cells as described above in addition to the staining process.

However, the evaluation results in the evaluation of whether the cells are the undifferentiated cells or the differentiated cells through the analyzing of the feature values of the cell image and the results in the staining process do not necessarily match each other.

Specifically, even though the evaluation of whether the cells are the undifferentiated cells or the differentiated cells is performed by analyzing the feature values of the cell image, in a case where a cell region or regions around the cell region is in a layered state, the staining marker hardly permeates within the cell, and the cell is not stained in some cases. In addition to such an example, even though the cells are evaluated as the undifferentiated cells by analyzing the cell image, in a case where the staining process is actually performed, it can be seen that the cells are not stained depending on the states of the cells of the regions around the cell region in some cases.

Predicting the staining states in a case where the staining process is performed is important in determining an operation for the cell and making a subsequent culture plan. JP2011-229409A does not suggest a method of predicting the staining states of the cells by using the image obtained by imaging the cells.

The present invention has been made in view of the aforementioned problems, and an object of the present invention is to provide a cell image evaluation device and a cell image evaluation program capable of recognizing staining states in which a staining process is performed on cells without performing the staining process and performing an operation such as subculturing and culture medium replacement for the cell at an appropriate timing.

A cell image evaluation device according to the present invention comprises: an evaluator that evaluates states of cells included in each region of interest for each region of interest of a cell image obtained by imaging cells, and outputs evaluation results; and a predictor that performs, in advance, machine learning of a relationship between evaluation results of the evaluator for regions around a specific region of interest within at least one first cell image obtained by imaging cells before a staining process and staining states of cells of the specific region of interest within a second cell image obtained by imaging the same imaging targets as the cells of the first cell image after the staining process. The predictor predicts staining states of cells of a specific region of interest based on evaluation results for regions around the specific region of interest among evaluation results of the evaluator for at least one third cell image obtained by imaging cells before the staining process, and outputs the predicted staining states.

In the cell image evaluation device according to the present invention, the predictor may output transition probabilities of two or more staining color intensities, as outputs of the staining states of the cells.

In the cell image evaluation device according to the present invention, the predictor may receive, as inputs, the evaluation results for the third cell image obtained by imaging an inside of a container that contains cells, and may output staining states of cells of a plurality of regions of interest within the container. The cell image evaluation device may further comprise an integration unit that integrates the staining states of the cells of each region of interest, and obtains staining states of the cells of the entire container.

In the cell image evaluation device according to the present invention, the predictor may output the transition probabilities of the two or more staining color intensities, as the outputs of the staining states of the cells, and the integration unit may integrate the transition probabilities of the two or more staining color intensities of each region of interest for each staining color intensity, and obtains the staining states of the cells of the entire container.

In the cell image evaluation device according to the present invention, the predictor may output the transition probabilities of the two or more staining color intensities, as the outputs of the staining states of the cells. The integration unit may integrate the staining color intensities of the highest transition probabilities of the transition probabilities of the two or more staining color intensities of each region of interest, and obtains the staining states of the cells of the entire container.

In the cell image evaluation device according to the present invention, the predictor may receive, as an input, at least one culture condition.

In the cell image evaluation device according to the present invention, the evaluator may evaluate at least whether the cells are in an undifferentiated state or a differentiated state.

In the cell image evaluation device according to the present invention, the evaluator may evaluate at least a density of nucleoli.

In the cell image evaluation device according to the present invention, the evaluator may evaluate at least a density of white streaks.

In the cell image evaluation device according to the present invention, the evaluator may evaluate at least whether the cells are fibroblasts or feeder cells.

In the cell image evaluation device according to the present invention, the evaluator may evaluate at least whether the cells are pluripotent stem cells or feeder cells.

In the cell image evaluation device according to the present invention, the evaluator may evaluate at least whether the cells are cells or non-cells.

In the cell image evaluation device according to the present invention, the evaluator may evaluate at least whether the cells are living cells or dead cells.

The cell image evaluation device according to the present invention may further comprise: an operation content determination unit that obtains information on the staining state of the cell output from the predictor, and determines an operation content for the cell based on the information on the staining state of the cell.

In the cell image evaluation device according to the present invention, it is preferable that the operation content for the cell is subculturing, culture medium replacement, culture medium change, agent addition, picking, or genetic testing.

A cell evaluation control program according to the present invention causes a computer to function as: an evaluator that evaluates states of cells included in each region of interest for each region of interest of a cell image obtained by imaging cells, and outputs evaluation results; and a predictor that performs, in advance, machine learning of a relationship between evaluation results of the evaluator for regions around a specific region of interest within at least one first cell image obtained by imaging cells before a staining process and staining states of cells of the specific region of interest within a second cell image obtained by imaging the same imaging targets as the cells of the first cell image after the staining process. The predictor predicts staining states of cells of a specific region of interest based on evaluation results for regions around the specific region of interest among the evaluation results of the evaluator for at least one third cell image obtained by imaging cells before the staining process, and outputs the predicted staining states.

In accordance with the cell image evaluation device and the cell image evaluation program according to the present invention, the evaluator that outputs the evaluation results obtained by evaluating the states of the cells for each region of interest of the cell image, and the predictor that performs, in advance, the machine learning of the relationship between the evaluation results of the evaluator for the regions around the specific region of interest within the first cell image obtained by imaging the cells before the staining process and the staining states of the cells of the specific region of interest within the second cell image obtained by imaging the same imaging targets as the cells of the first cell image after the staining process are provided.

Since the predictor predicts staining states of cells of a specific region of interest based on evaluation results for regions around the specific region of interest among the evaluation results of the evaluator for the third cell image obtained by imaging the cells before the staining process and outputs the predicted staining states, it is possible to recognize the staining states in which the staining process is performed on the cells without performing the staining process, and it is possible to perform an operation such as subculturing and culture medium replacement for the cell at an appropriate timing.

BRIEF DESCRIPTION OF THE DRAWINGS

FIG. 6 is an explanatory diagram for describing an example of the machine learning method of the predictor.

DESCRIPTION OF THE PREFERRED EMBODIMENTS

Figure 1:
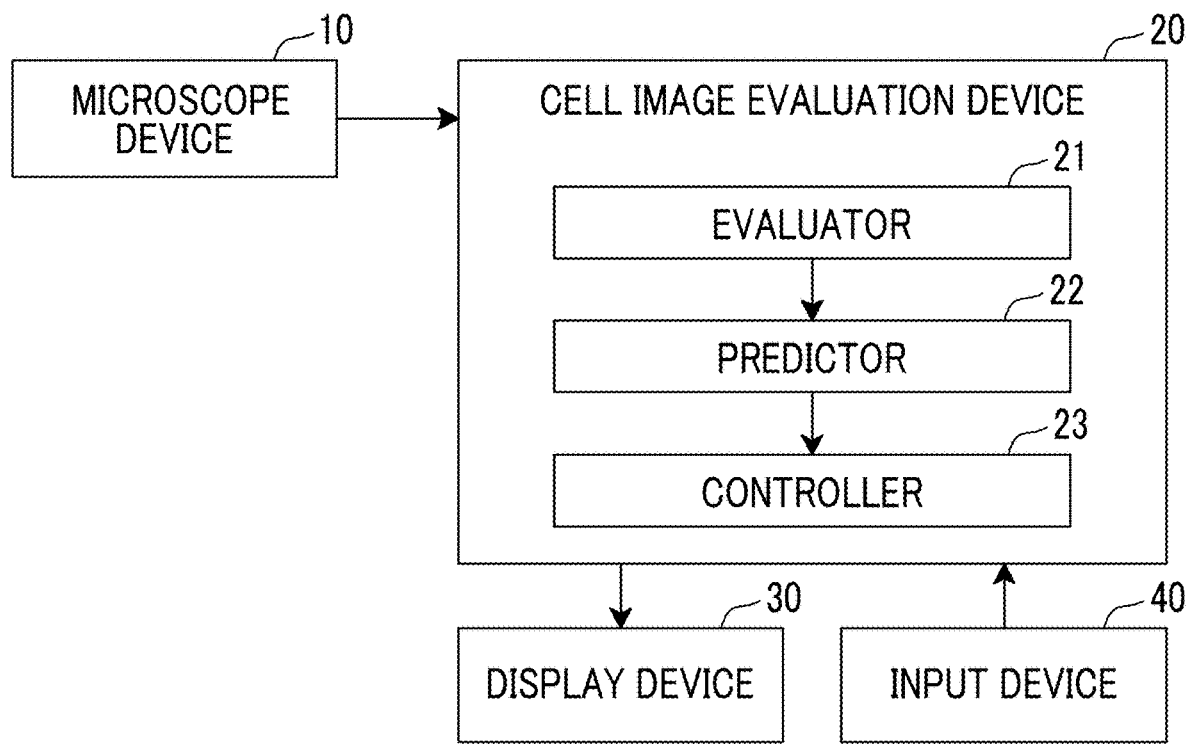
FIG. 1 is a block diagram showing a schematic configuration of a cell image evaluation prediction system using an embodiment of a cell image evaluation device according to the present invention.

Hereinafter, a cell image evaluation prediction system using embodiments of a cell image evaluation device and a cell image evaluation program according to the present invention will be described in detail with reference to the drawings. FIG. 1 is a block diagram showing a schematic configuration of the cell image evaluation prediction system of the present embodiment.

The cell image evaluation prediction system of the present embodiment comprises a microscope device 10, a cell image evaluation device 20, a display device 30, and an input device 40, as shown in FIG. 1.

The microscope device 10 images cells contained in a culture container, and outputs a cell image. Specifically, a phase difference microscope device comprising an imaging element such as a charge-coupled device (CCD) image sensor or a complementary metal-oxide semiconductor (CMOS) image sensor is used in the present embodiment. As the imaging element, an imaging element in which red, green, and blue (RGB) color filters are provided may be used, or a monochrome imaging element may be used. A phase difference image of the cells contained in the culture container is formed on the imaging element, and the phase difference image is output as the cell image from the imaging element. The microscope device 10 is not limited to the phase difference microscope device, and other microscope devices such as a differential interference microscope device and a bright-field microscope device may be used.

The cell image may be an image obtained by imaging a cell colony in which a plurality of cells is aggregated or an image in which a plurality of cells is dispersedly distributed. In the present embodiment, pluripotent stem cells such as iPS cells and ES cells and cells of nerve, skin, cardiac muscle, and liver differentiated and induced from stem cells may be captured as imaging targets.

In the present embodiment, the cells as the imaging targets are contained in a well plate with multiple wells. The microscope device 10 comprises a stage moving in an X direction and a Y direction which cross each other within a horizontal plane, and the well plate is provided on the stage. Parts to be observed within the well plate are scanned while moving the stage in the X direction and the Y direction, and thus, cell images for the parts to be observed are captured. The cell images for the parts to be observed are combined as one cell image, and the one cell image is output to the cell image evaluation device 20. Although the well plate is used in the present embodiment, the container in which the cell is contained is not limited thereto. For example, other containers such as petri dishes or dishes may be used.

As shown in FIG. 1, the cell image evaluation device 20 comprises an evaluator 21, a predictor 22, and a controller 23. The cell image evaluation device 20 is a computer comprising a central processing unit, a semiconductor memory, and a hard disk, and the embodiment of the cell image evaluation program according to the present invention is installed in the hard disk. The cell image evaluation program is executed by the central processing unit, and thus, the evaluator 21, the predictor 22, and the controller 23 shown in FIG. 1 function.

Figure 2:
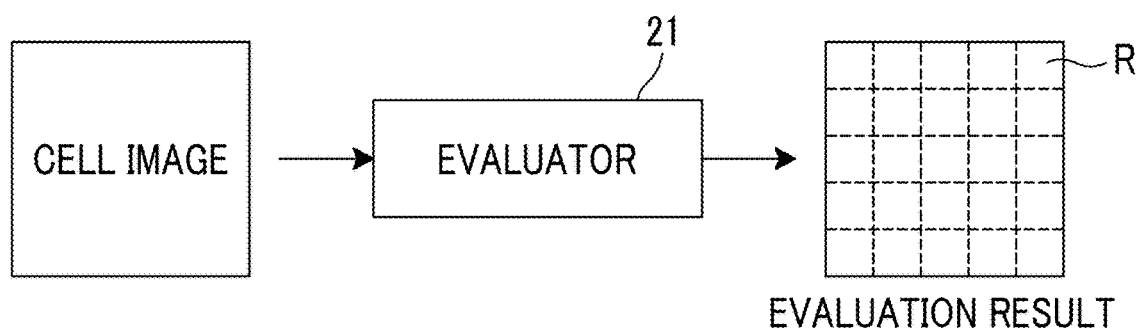
FIG. 2 is an explanatory diagram for describing an evaluator.

The evaluator 21 obtains the cell image output from the microscope device 10, and evaluates states of the cells included in the obtained cell image. Specifically, the evaluator 21 divides the input cell image into a plurality of regions R of interest as shown in FIG. 2, evaluates the states of the cells included in cell images of the regions R of interest, and outputs evaluation results for the regions R of interest. A rectangular region represented by a dotted line in FIG. 2 is the region R of interest. Although the part to be observed by the microscope device 10 and the region of interest are the same region in the present embodiment, the present invention is not limited thereto. The region R of interest may be set to be wider than the part to be observed, or the region R of interest may be set to be narrower than the part to be observed.

The evaluator 21 of the present embodiment evaluates whether the cells included in the cell image are differentiated cells or are not undifferentiated cells based on the cell image of each region R of interest. The evaluator 21 evaluates whether the cell image of each region R of interest is an image of only a culture medium without including the cell, evaluates the density of white streaks (cracks) included in the cell image, and evaluates whether or not the cells included in the cell image are in a layered state. The evaluator 21 outputs any one of "region of undifferentiated cells (cells in undifferentiated state)", "region of differentiated cells (cells in differentiated state)", "region in which white streaks are densely present", "region in which cells are in layered state", and "culture medium region", as the evaluation result of each region of interest. The white streaks (cracks) are blurring (halo) of light due to diffracted light generated between the cells and a background.

Figure 3:
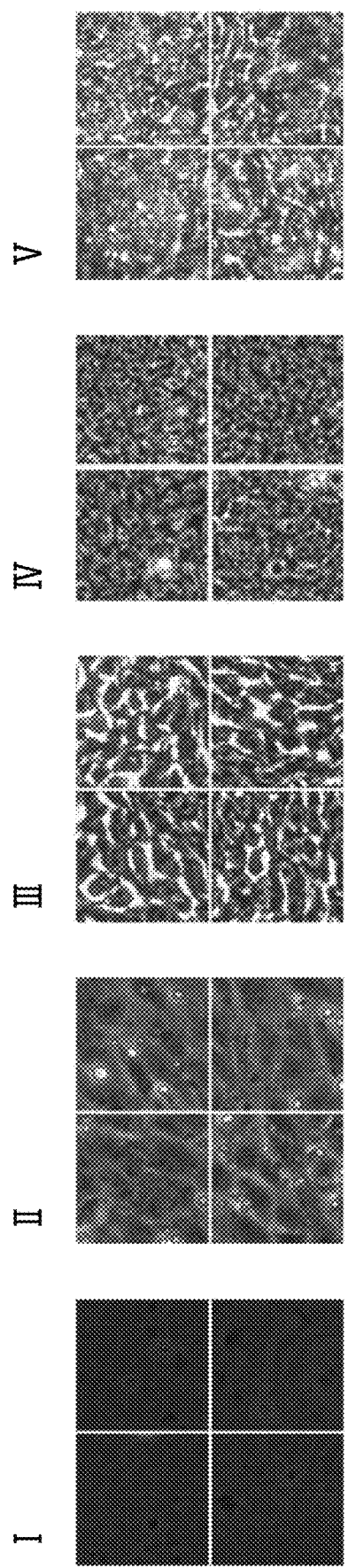
FIG. 3 is a diagram showing examples of cell images obtained by imaging various states of cells.

I of FIG. 3 shows an example of the image of the culture medium, II of FIG. 3 shows an example of the cell image of the differentiated cells, III of FIG. 3 shows an example of the cell image on which the density of the white streaks is high, IV of FIG. 3 shows an example of the cell image of the undifferentiated cells, and V of FIG. 3 shows an example of the cell image on which the cells are in the layered state.

For example, the evaluation of whether the cells included in the cell image are the differentiated cells or the undifferentiated cells can be performed by extracting single cells one by one from the cell image and evaluating degrees of circularity of the single cells. Specifically, the degree of circularity of the undifferentiated cell becomes relatively high, and the degree of circularity thereof becomes relatively low since the differentiated cell has an elongated shape. Accordingly, the evaluator can evaluate whether the cells are the differentiated cells or the undifferentiated cells by calculating the degrees of circularity of the single cells. A known image processing method such as an edge detection process can be used as the method of extracting the single cells from the cell image.

The method of evaluating whether the cells are the differentiated cells or the undifferentiated cells is not limited to the evaluation based on the degrees of circularity of the single cells. The evaluation may be performed by using the number (density) of single cells per unit area, the number (density) of nucleoli per unit area, and an average area of the single cells. The density of the single cells in the undifferentiated cells tends to be higher than in the differentiated cells. Similarly, the density of the nucleoli in the undifferentiated cells also tends to be higher than in the differentiated cells. The average area of the single cells in the differentiated cells tends to be larger than in the undifferentiated cells. The method of evaluating whether the cells are the differentiated cells or the undifferentiated cells is not limited to the aforementioned evaluation method, and other known evaluation methods may be used.

As the evaluation of whether the region of interest is the culture medium region, the evaluator may extract the single cells from the cell images of the regions of interest, and may evaluate that the region of interest is the culture medium region in a case where the number of single cells is equal to or less than a preset threshold value, for example.

As the evaluation of the density of the white streaks included in the cell image of the region of interest, the evaluator may perform a binarization process on the cell image, may extract a white pixel region in which white pixels are elongated and continuously present from the image after the binarization process, and may calculate the density in the area thereof, for example. In a case where the calculated density of the white pixel region is equal to or greater than the preset threshold value, the evaluator may evaluate that the region of interest is the region in which the white streaks are densely present.

In the evaluation of whether the cells included in the cell image are in the layered state, in a case where the cells are in the layered state, a density level of the cells becomes high, and brightness of the cell image becomes high. Accordingly, the evaluator may obtain a brightness distribution of the cell image, and may evaluate that the cells are in the layered state in a case where an average value of brightness is larger than a preset threshold value. Alternatively, the evaluator may evaluate whether or not the cells are in the layered state by analyzing a spatial frequency of the brightness distribution of the cell image. Other known methods can be used as the evaluation method of whether or not the cells are in the layered state.

Subsequently, the predictor 22 receives, as inputs, evaluation results of the evaluator 21 for at least one cell image obtained by imaging the cells after a staining process, predicts staining states of the cells in the specific region of interest based on evaluation results of the evaluator 21 for a specific region of interest within the cell image and regions around the specific region of interest, and outputs the predicted stained states.

Here, as described above, the staining process is a process for checking whether or not the pluripotent stem cells are maintained in the differentiated state or whether or not the undifferentiated cell is included in a desired cell in a case where the desired cell is differentiated and induced. For example, and a staining marker such as alkaline phosphatase is used. The undifferentiated cell is stained and the differentiated cell is not stained depending on the kind of alkaline phosphatase.

In a case where the staining process is performed, the result of the staining process of whether or not the cell is stained and the evaluation result of whether or not the cell is the undifferentiated cell or the differentiated cell do not necessarily match each other. Specifically, for example, even though the evaluator evaluates that the cells within the predetermined region of interest are the undifferentiated cells, in a case where the cells in the region of interest or the regions around the region of interest are in the layered state, since the staining marker hardly permeates within the cell, the cell is not stained in some cases. The present invention is not limited to such an example. Even though the evaluator evaluates that the cells within the region of interest are the undifferentiated cells, in a case where the staining process is actually performed, it can be seen that the cell is not stained depending on the states of the cells in the regions around the region of interest in some cases.

Thus, as stated above, the predictor 22 of the present embodiment predicts the staining states of the cells in the specific region of interest based on the evaluation results of the evaluator 21 for the specific region of interest within the cell image and the regions around the specific region of interest, and outputs the predicted staining states.

Figure 4:
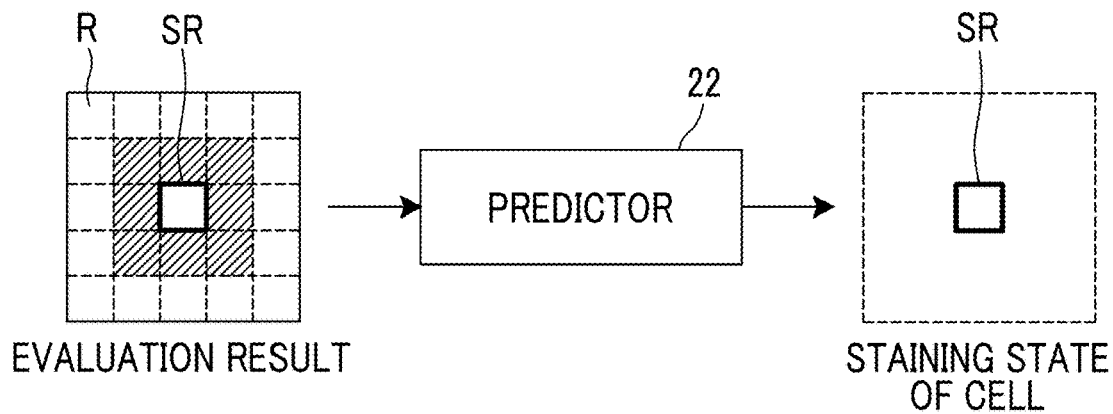
FIG. 4 is an explanatory diagram for describing a predictor.
Figure 5:
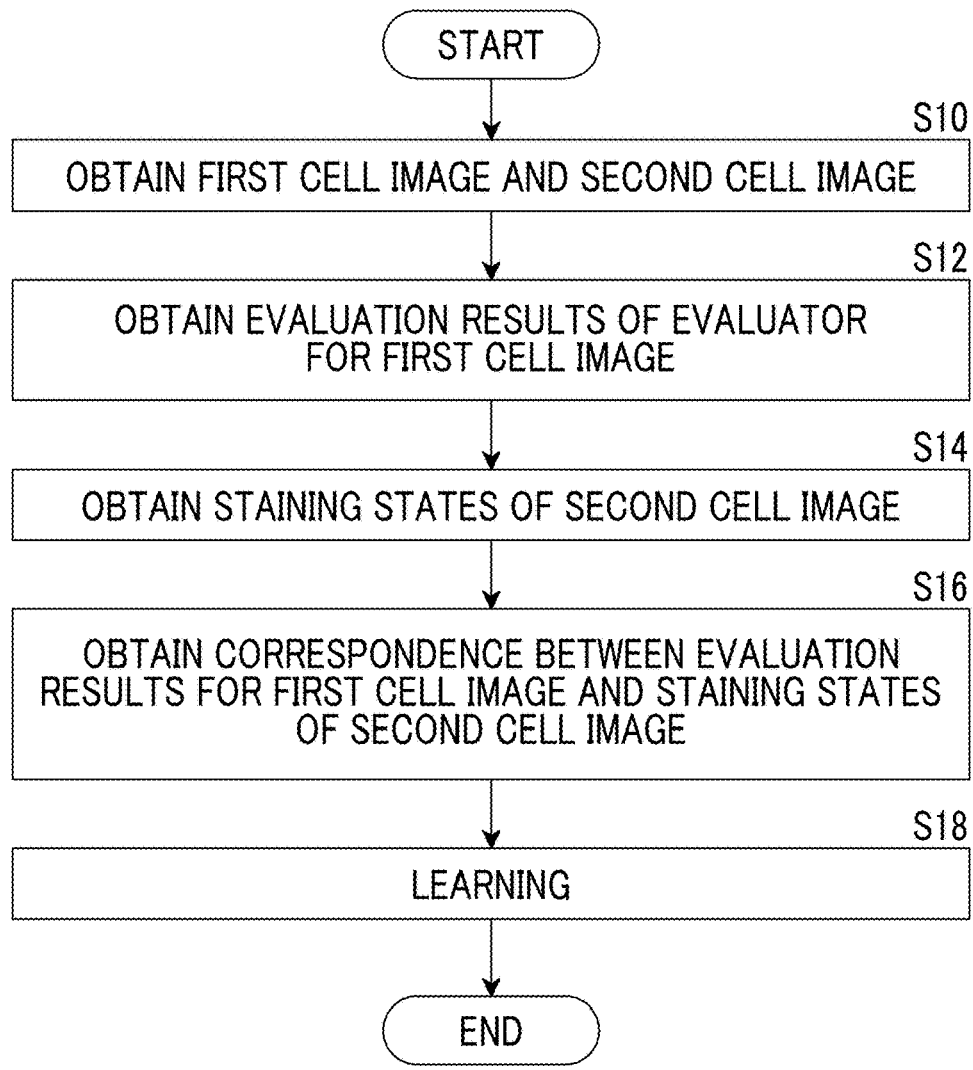
FIG. 5 is a flowchart for describing an example of a machine learning method of the predictor.
Figure 7:
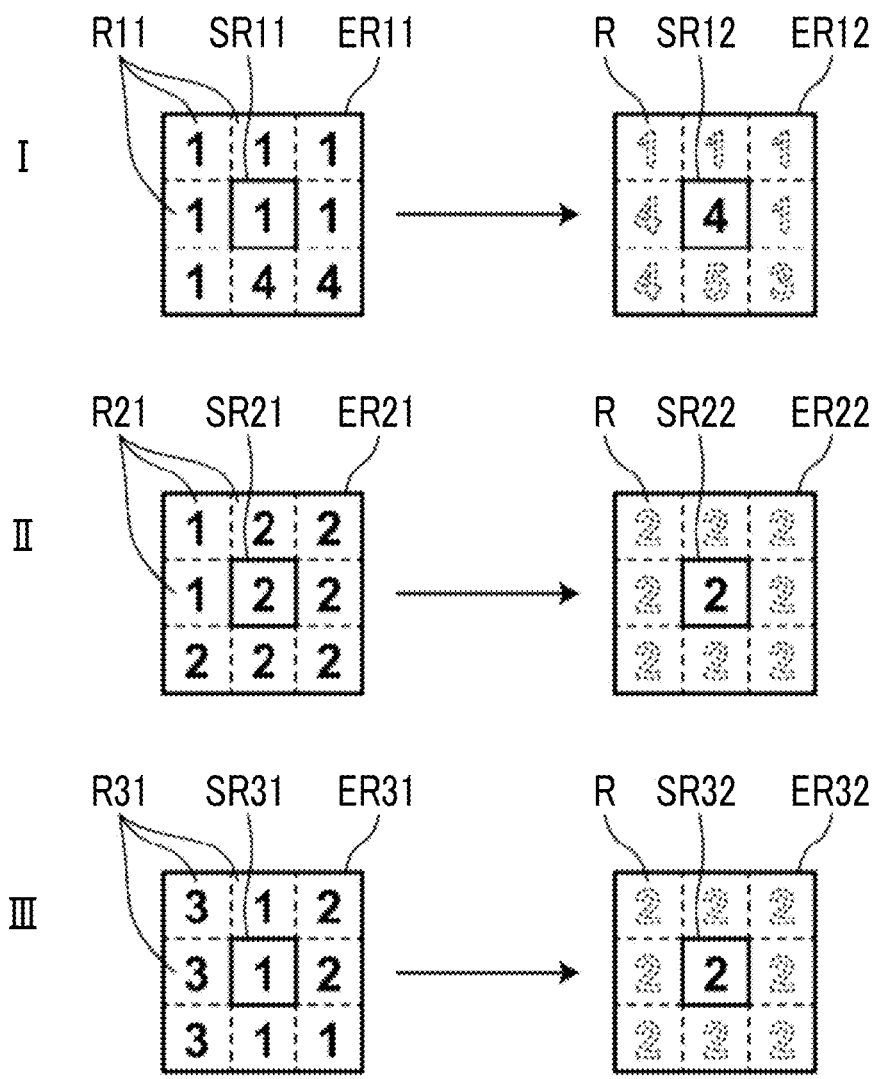
FIG. 7 is an explanatory diagram for describing an example of the machine learning method of the predictor.

Specifically, the predictor 22 receives, as inputs, the evaluation results for the regions R of interest on the cell image obtained by imaging the cells after the staining process, as shown in FIG. 4. The predictor 22 predicts the staining states of the cells included in the specific region SR of interest based on the evaluation results for a specific region SR of interest of the plurality of regions R of interest within the cell image and the region R of interest of the specific region SR of interest which are input, and outputs the predicted staining states. In FIG. 4, the regions R of interest around the specific region of interest are depicted by a diagonal line.

The predictor 22 performs machine learning in advance such that the staining states thereof are predicted for the cells on which the staining process is not actually performed on the assumption that the staining process is performed and the predicted staining states are output. Specifically, the predictor 22 performs, in advance, machine learning of a relationship between evaluation results for a specific region of interest within a first cell image obtained by imaging the cells before the staining process and regions around the specific region of interest and staining states of cells in the specific region of interest within a second cell image obtained by imaging the same imaging targets as the cells of the first cell image after the staining process. Hereinafter, an example of the method of the machine learning of the predictor 22 will be described with reference to a flowchart shown in FIG. 5 and FIGS. 6 to 8.

Initially, the first cell image obtained by imaging the cells before the staining process and the second cell image after the staining process are obtained (S10), the first cell image is input to the evaluator 21, and the evaluation results for the regions R of interest described above are obtained (S12). I of FIG. 6 is a diagram showing an example of the evaluation results for the regions R of interest within the first cell image before the staining process. In I of FIG. 6, the evaluation result of "culture medium region" is "1", the evaluation result of "region of differentiated cells" is "2", the evaluation result of "region in which white streaks are densely present" is "3", the evaluation result of "region of undifferentiated cells" is "4", and the evaluation result of "region in which cells are in layered state" is "5".

Subsequently, the staining states of the regions R of interest of the second cell image after the staining process are obtained (S14). The images of the regions R of interest of the second cell image may be evaluated, and the staining states of the second cell image may be classified according to staining intensities. The evaluator 21 may perform the evaluation based on brightness information of the second cell image, or a device different from the cell image evaluation prediction system of the present embodiment may perform the evaluation. Alternatively, a user may evaluate the staining states, and may set and input the evaluation results thereof by using the input device 40.

II of FIG. 6 is a diagram showing an example of the staining states of the cells of the regions R of interest of the second cell image. In II of FIG. 6, staining color intensities obtained through the staining process are represented as five stages, and a staining state "1" means no color, and a staining state "5" means that the staining color intensity is the highest.

Figures 8, 9:
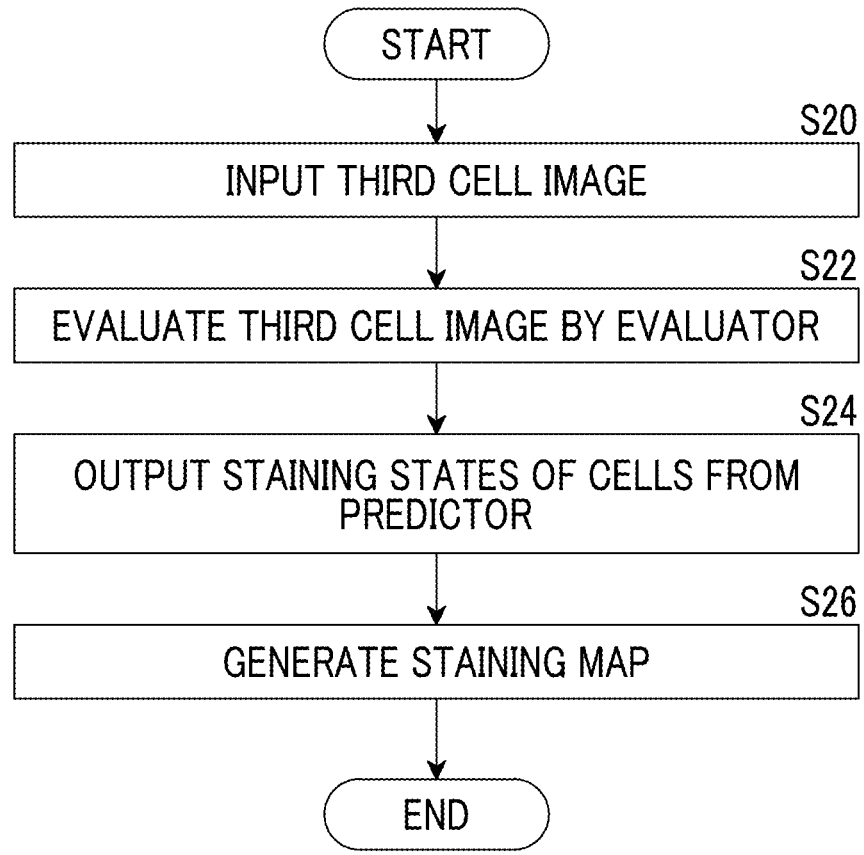
FIG. 8 is an explanatory diagram for describing an example of the machine learning method of the predictor.
FIG. 9 is a flowchart for describing a method of predicting staining states of the cells by using the predictor that performs machine learning.

A correspondence between the evaluation results for the first cell image shown in I of FIG. 6 and the staining state of the second cell image shown in II of FIG. 6 is obtained (S16), and the predictor 22 performs machine learning of the correspondence (S18). Specifically, a region ER11 of 3×3 regions of interest shown in I of FIG. 6 and a region ER12 of the second cell image corresponding to the region ER11 are specified, for example. As shown in I of FIG. 7, evaluation results for a specific region SR11 of interest positioned in the center of the region ER11 and regions R11 of interest around the specific region and a staining state of a specific region SR12 of interest positioned in the center of a region ER12 correspond to each other, and the predictor 22 performs machine learning of this correspondence. More specifically, as shown in FIG. 8, learning feature values obtained by arranging the evaluation results for the regions R of interest of the region ER11 in order from the evaluation result positioned in the upper left region toward the evaluation result positioned in the lower right region are obtained, and the staining state of the specific region SR12 of interest of the region ER12 is obtained as a learning class corresponding to this learning feature values. The predictor 22 performs machine learning of a relationship between the learning feature values and the learning classes shown in FIG. 8.

Similarly, a region ER21 of 3×3 regions of interest shown in I of FIG. 6 and a region ER22 of the second cell image corresponding to the region ER21 are specified. As shown in II of FIG. 7, evaluation results for a specific region SR21 of interest positioned in the center of the region ER21 and regions R21 of interest around the specific region of interest and a staining state of a specific region SR22 of interest positioned in the center of the region ER22 correspond to each other, and the predictor 22 performs machine learning of this correspondence. Specifically, as shown in FIG. 8, learning feature values obtained by arranging the evaluation results for the regions R of interest of the region ER21 in order from the evaluation result positioned in the upper left region toward the evaluation result positioned in the lower right region are obtained, and the staining state of the specific region SR22 of interest of the region ER22 is obtained as a learning class corresponding to the learning feature values. The predictor 22 performs machine learning of a relationship between the learning feature values and the learning classes shown in FIG. 8.

Similarly, a region ER31 of 3×3 regions of interest shown in I of FIG. 6 and a region ER32 of the second cell image corresponding to the region ER31 are specified. As shown in III of FIG. 7, evaluation results for a specific region SR31 of interest positioned in the center of the region ER31 and regions R31 of interest around the specific region of interest and an evaluation result of a specific region SR32 of interest positioned in the center of the region ER32 correspond to each other, and the predictor 22 performs machine learning of this correspondence. As shown in FIG. 8, learning feature values of the region ER31 and a staining state of the specific region SR32 of interest of the region ER32 are obtained as a learning class corresponding to the learning feature values. The predictor 22 performs machine learning of a relationship between the learning feature values and the learning classes shown in FIG. 8.

Although it has been described that the machine learning of the correspondence between the evaluation results for the three regions is performed, the predictor 22 performs machine learning of a correspondence between staining states and evaluation results for a plurality of other regions in addition to the three regions. Although it has been described the correspondence between the staining states and the evaluation results for the 3×3 regions of interest is used, the present invention is not limited to the 3×3 regions of interest. For example, machine learning may be performed by using a correspondence between staining states and evaluation results for 5×5 regions of interest.

A support vector machine (SVM), a deep neural network (DNN), a convolution neural network (CNN), a recurrent neural network (RNN), and a denoising stack auto encoder (DSA) can be used as the machine learning method.

The first cell image and the second cell image used in a case where the predictor 22 performs the machine learning may not be necessarily captured by the microscope device 10. Alternatively, cell images stored in an external server device other than the cell image evaluation prediction system of the present embodiment may be used.

FIG. 9 is a flowchart for describing a method of predicting the staining state of the cell by using the predictor that has performed the machine learning as described above.

As shown in FIG. 9, a third cell image before the staining process which is captured by the microscope device 10 and is input to the evaluator 21 (S20). States of cells of regions R of interest of the third cell image are evaluated by the evaluator 21 (S22).

Subsequently, evaluation results for the regions R of interest of the third cell image are input to the predictor 22. As shown in FIG. 4, the predictor 22 predicts a staining state of the cell of the specific region SR of interest based on the evaluation result of the specific region SR of interest within the third cell image and the evaluation results for the regions R of interest around the specific region of interest (S24).

The predictor 22 of the present embodiment sets each region R of interest within the third cell image as the specific region SR of interest, similarly predicts the staining state of the cell for the entire third cell image, and generates a staining map using the aforementioned learning classes as the staining states (S26).

Referring back to FIG. 1, the controller 23 controls the entire cell image evaluation device 20. The controller 23 displays the staining map generated by the predictor 22 on the display device 30. In the present embodiment, the third cell image for each well is input to the evaluator 21, and the staining map for each well is generated based on the evaluation results thereof. As the staining map, a color map in which the staining states are color-coded based on, for example, magnitudes of the predicted staining color intensities may be generated, and the generated color map may be displayed on the display device 30.

The cell image evaluation prediction system of the aforementioned embodiment comprises the evaluator 21 that outputs the evaluation results obtained by evaluating the states of the cells for each region of interest obtained by dividing the cell image into the plurality of regions, and the predictor 22 that performs, in advance, the machine learning of the relationship between the evaluation results of the evaluator 21 for the specific region of interest within the first cell image obtained by imaging the cells before the staining process and the regions around the specific region of interest and the staining states of the cells of the specific region of interest within the second cell image obtained by imaging the same imaging targets as the cells of the first cell image after the staining process.

Since the predictor 22 receives, as the input, the evaluation results of the evaluator for the third cell image obtained by imaging the cell before the staining process, predicts the staining states of the cells in the specific region of interest based on the evaluation results of the evaluator 21 for the specific region of interest within the third cell image and the regions around the specific region of interest, and outputs the predicted staining states, it is possible to recognize the staining states in which the staining process is performed on the cells without performing the staining process, and it is possible to perform an operation such as subculturing and culture medium replacement for the cell at an appropriate timing.

Since the predictor 22 that has performed the machine learning predicts the staining states, staining prediction results based on evaluation results for a plurality of past staining states are obtained, and whether the cells are undifferentiated or differentiated is simply determined for the current cell image. Accordingly, it is possible to obtain results more reliable than a color-coded image in which the states of the cells are color-coded based on the determination result.

In the present embodiment, the evaluation of the evaluator 21 for the first cell image and the third cell image may include the density of the nucleoli. In the case of the undifferentiated cells, since the cells are aggregated and the colony is formed, the density of the nucleoli is high. In the case of the differentiated cells, since the cells are separated and distributed, the density of the nucleoli is low. Accordingly, it is possible to improve accuracy of the prediction results of the predictor 22 by including the density of the nucleoli as the evaluation of the evaluator 21.

In the present embodiment, the predictor 22 that has performed, in advance, the machine learning of the relationship between the evaluation results of the evaluator 21 for the specific region of interest within the first cell image obtained by imaging the cells before the staining process and the regions around the specific region of interest and the staining states of the cells of the specific region of interest within the second cell image obtained by imaging the same imaging targets as the cells of the first cell image after the staining process is provided. The predictor 22 receives, as the input, the evaluation results of the evaluator 21 for the third cell image obtained by imaging the cells before the staining process, predicts the staining states of the cells of the specific region of interest based on the evaluation results of the evaluator 21 for the specific region of interest within the third cell image and the regions around the specific region of interest, and outputs the predicted staining states. That is, the predictor performs the machine learning by using the evaluation results for the specific region of interest and the evaluation results for the regions around the specific region of interest, predicts the staining states of the cells of the specific region of interest by using the evaluation for the specific region of interest and the evaluation results for the regions around the specific region of interest, and outputs the predicted staining states. However, in a case where the predictor 22 performs the machine learning, only the evaluation results for the regions around the specific region of interest may be used as the evaluation results for the cells before the staining process without using the evaluation results for the specific region of interest. In a case where the predictor 22 predicts the staining states of the cells of the specific region of interest and outputs the predicted staining states, only the evaluation results for the regions around the specific region of interest may be used without using the evaluation results for the specific region of interest.

That is, the predictor 22 that has performed, in advance, the machine learning of the relationship between the evaluation results of the evaluator 21 for the regions around the specific region of interest within the first cell image obtained by imaging the cells before the staining process and the staining states of the cells of the specific region of interest within the second cell image obtained by imaging the same imaging targets as the cells of the first cell image after the staining process may be provided. The predictor may predict the staining states of the cells of the specific region of interest based on the evaluation results of the evaluator 21 of the regions around the specific region of interest within the third cell image obtained by imaging the cells before the staining process, and may output the predicted staining states.

Figure 10:
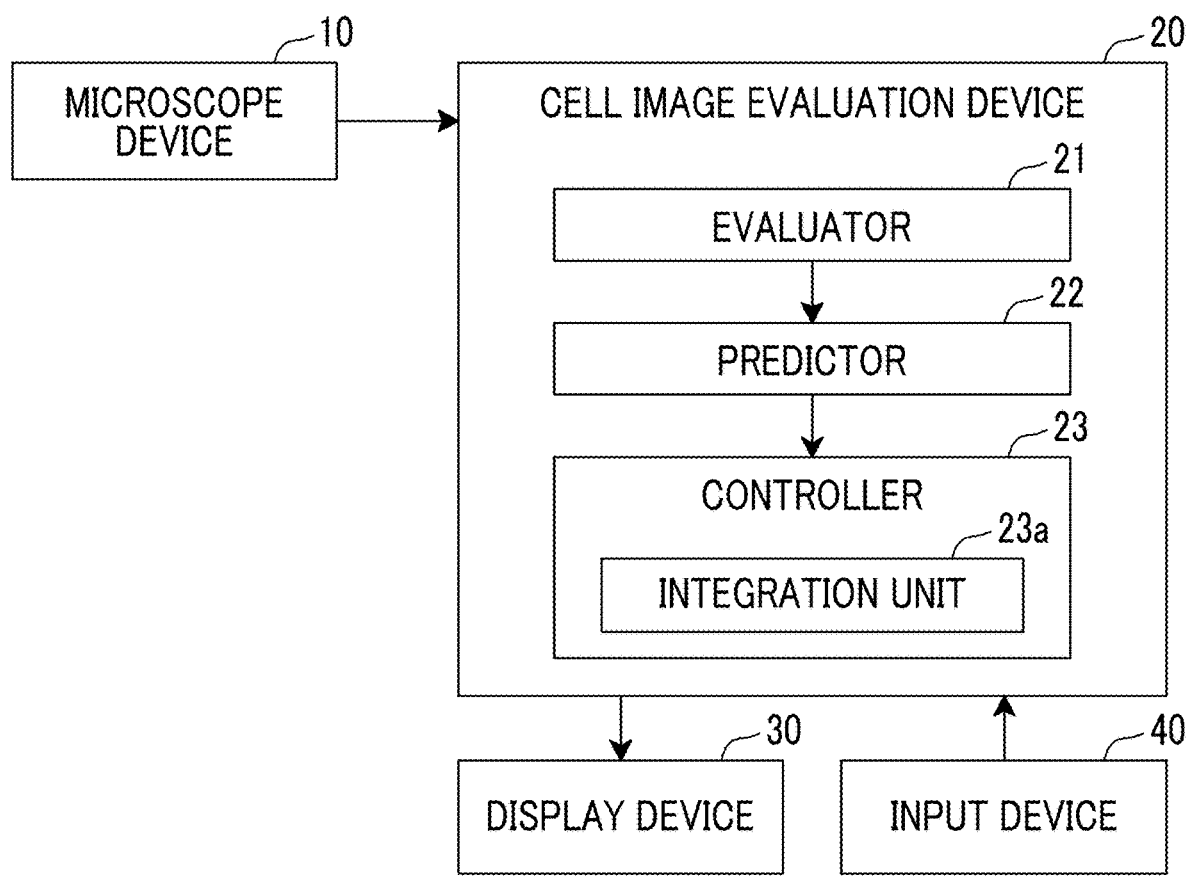
FIG. 10 is a block diagram showing a schematic configuration of a cell image evaluation prediction system using another embodiment of the cell image evaluation device according to the present invention.

Although it has been described in the aforementioned embodiment that the staining map for each well generated by the predictor 22 is displayed on the display device 30, the present invention is not limited thereto. The prediction results for the regions of interest output from the predictor 22 may be integrated, an index indicating the staining states of the cells of the entire well may be calculated, and the calculated index may be displayed on the display device 30. FIG. 10 is a block diagram showing a schematic configuration of the cell image evaluation prediction system including an integration unit 23*a* that integrates the prediction results for the regions of interest, and obtains the index indicating the staining states of the cells of the entire well as stated above.

For example, the integration unit 23*a* calculates a ratio of the region of each staining color intensity to the entire well, and displays this ratio as the index indicating the staining states of the cells of the entire well together with the staining map on the display device 30. Alternatively, a ratio of a region having a specific staining color intensity, for example, a staining color intensity of "4" or more to the entire well may be calculated, or the calculated ratio together with the staining map may be displayed on the display device 30.

Although it has been described in the aforementioned embodiment that the staining states are output from the predictor 22, the present invention is not limited thereto. Transition probabilities of two or more staining color intensities of the cells included in the region of interest may be output from the predictor 22. Specifically, for example, the predictor 22 may be configured to output the transition probabilities of the staining color intensities (simply represented as emission intensities in FIG. 11) for each region R of interest as shown in FIG. 11.

Figure 11:
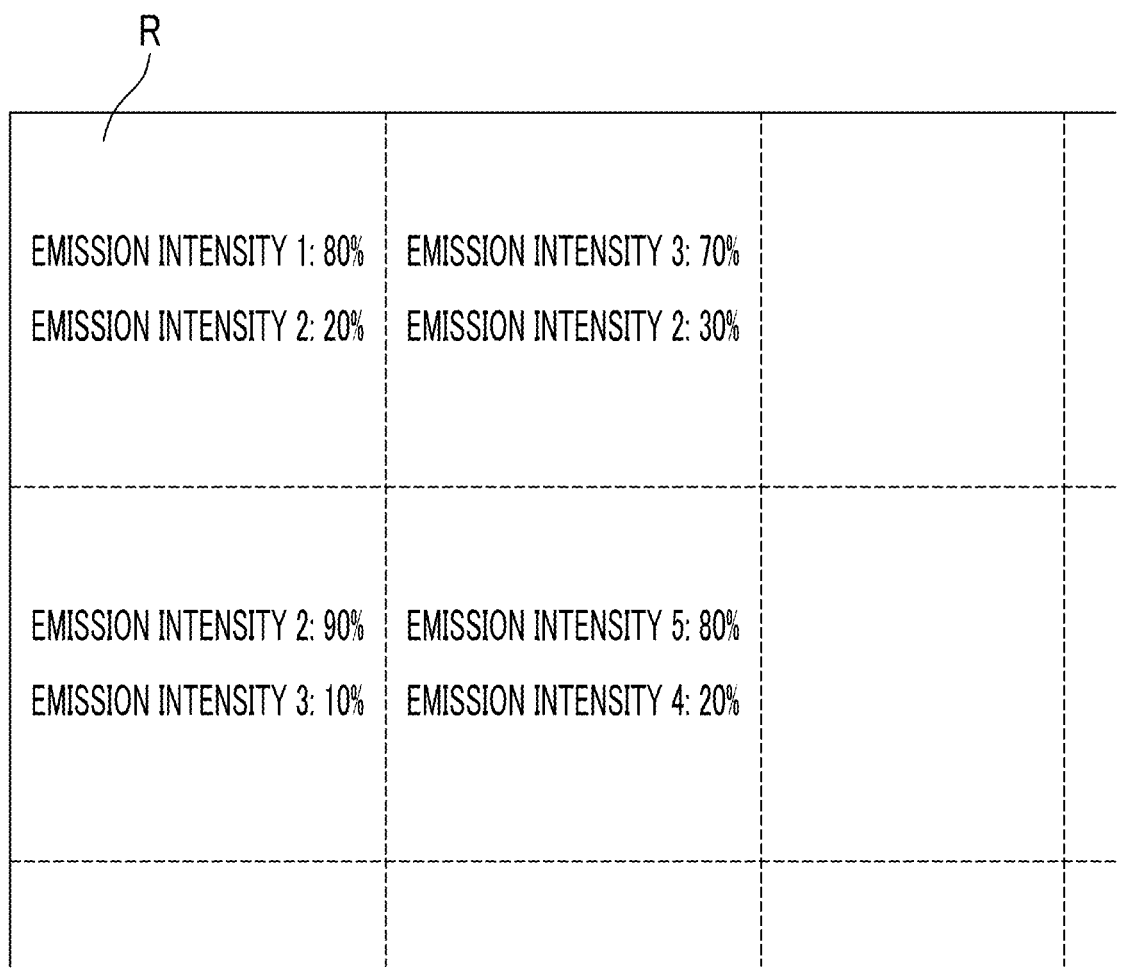
FIG. 11 is a diagram showing an example of transition probabilities of staining emission intensities of each region of interest.

As shown in FIG. 11, a prediction map may be generated by mapping two or more transition probabilities of each region of interest output from the predictor 22, and the generated prediction map may be displayed on the display device 30. Alternatively, the integration unit 23*a* may integrate the two or more transition probabilities of each region of interest, and may obtain the staining states of the cells of the entire well.

As the method of integrating the two or more transition probabilities of each region of interest in the integration unit 23*a*, the highest transition probabilities of the two or more transition probabilities of each region of interest may be integrated, for example. Specifically, as shown in FIG. 11, in a case where the predictor 22 outputs the transition probabilities of the staining emission intensities for each region R of interest, the staining emission intensity of the higher transition probability of the two transition probabilities of each region R of interest is obtained as the staining emission intensity of each region R of interest. For example, in a case where a transition probability of a staining emission intensity "1" is 80% and a transition probability of a staining emission intensity "2" is 20% in a predetermined region R of interest, it is assumed that a staining state of the cells of the predetermined region R of interest is the staining emission intensity "1". Similarly, the staining emission intensity is specified for another region R of interest within the well. The staining state of the cells of the entire well is obtained by calculating a ratio of the number of regions R of interest of each staining emission intensity to the number of regions R of interest of the entire well.

Alternatively, the highest transition probabilities of the two or more transition probabilities of each region of interest may not be integrated as stated above, and the transition probabilities of each region of interest may be integrated in the entire well. Specifically, the transition probabilities of the staining emission intensities may be obtained for the entire well by respectively adding the transition probabilities of the staining emission intensities added to the staining emission intensities for each region of interest within the well and dividing the added probability by the number of regions of interest of the entire well.

Figure 12:
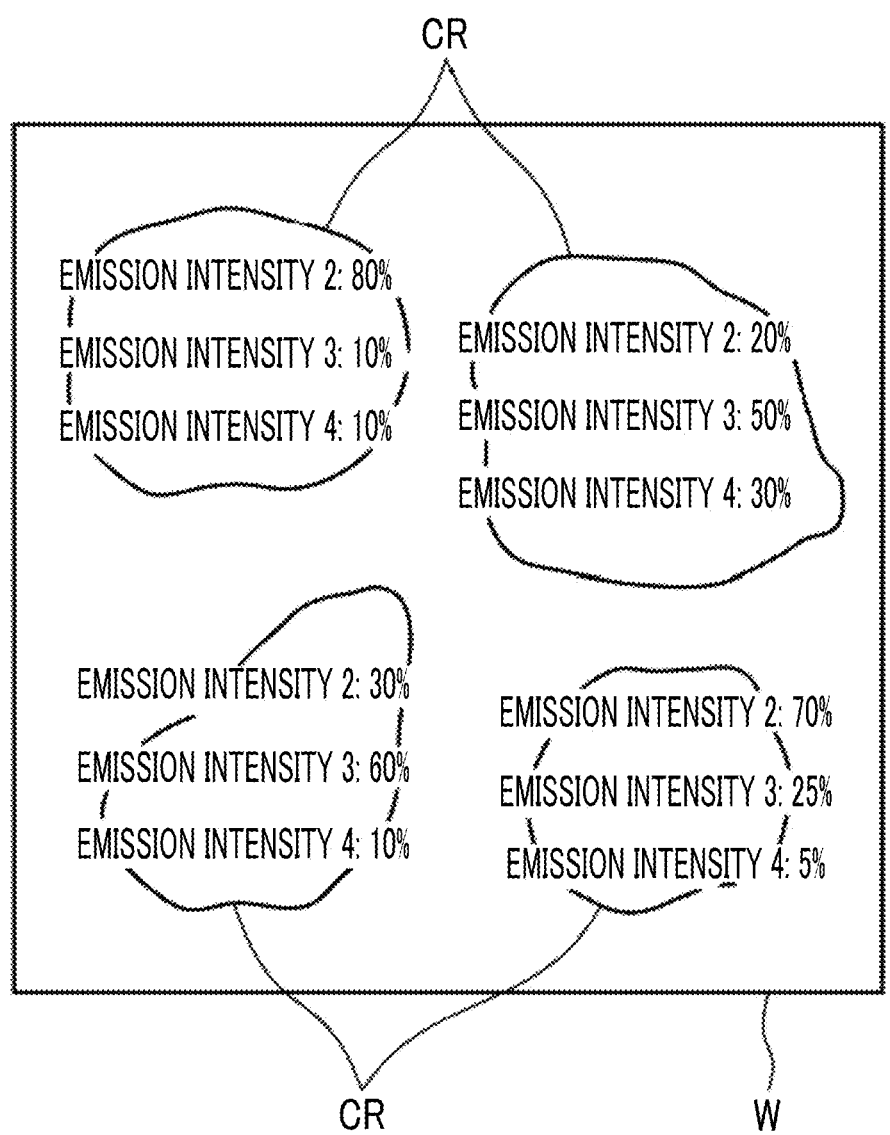
FIG. 12 is a diagram showing an example in which transition probabilities of staining emission intensities are integrated for each cell colony region within a well.

The transition probabilities of the staining emission intensities may not be integrated for the entire well, and the transition probabilities of the staining emission intensities on a cell colony basis may be integrated. FIG. 12 shows an example in which transition probabilities of staining emission intensities (simply represented as emission intensities in FIG. 12) are integrated for each cell colony region CR within a well W. A transition probability map shown in FIG. 12 may be generated, and the generated map may be displayed on the display device 30.

Figure 13:
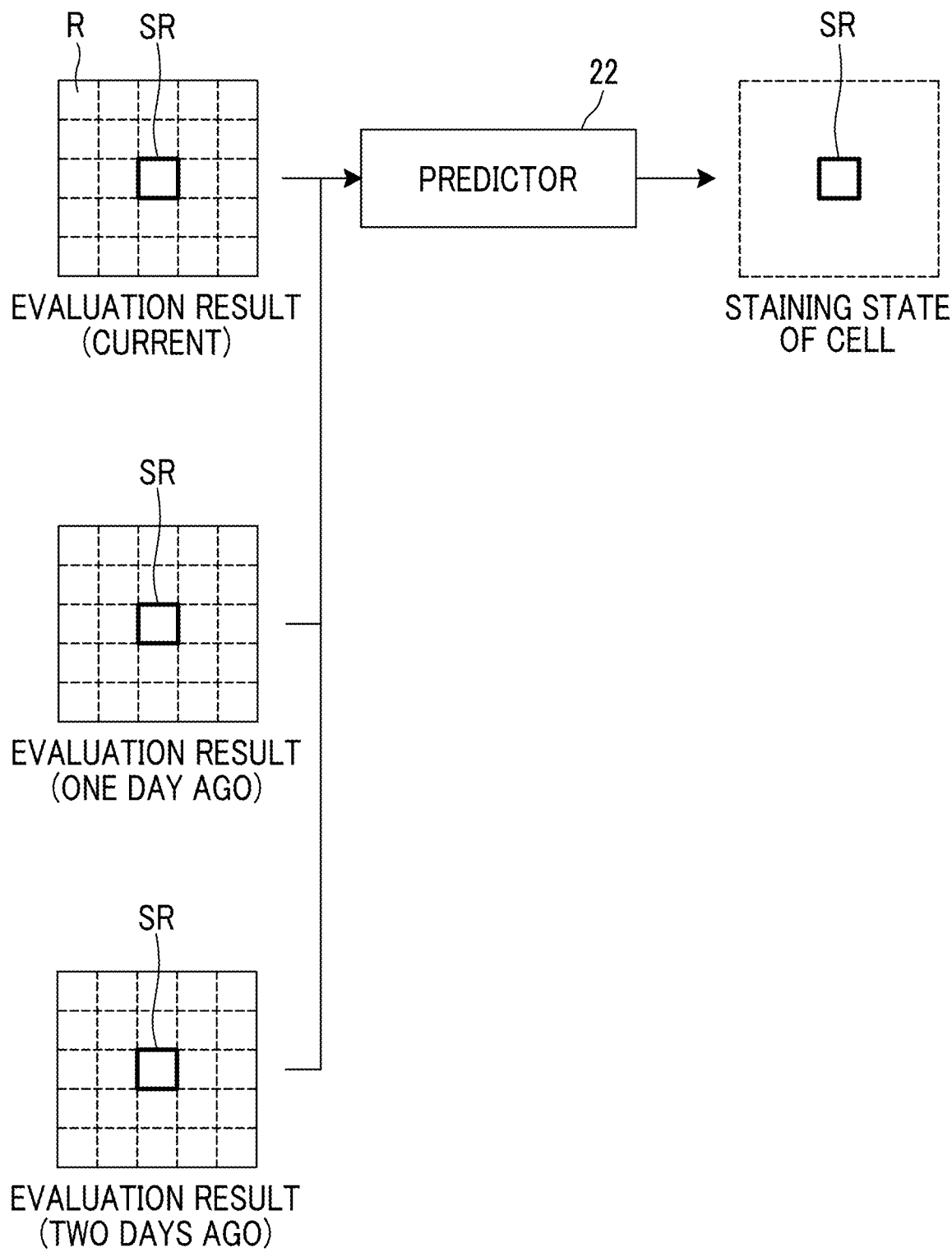
FIG. 13 is a diagram showing an example in which evaluation results for a plurality of third cell images captured at different points of time are input to the predictor and one prediction result is obtained.

Although it has been described in the aforementioned embodiment that the evaluation results for one third cell image are input to the predictor 22, the present invention is not limited thereto. Evaluation results for third cell images captured at multiple different points of time may be input. FIG. 13 is a diagram showing an example in which an evaluation result of a third cell image captured at a current point of time, an evaluation result of a third cell image captured one day ago, and an evaluation result of a third cell image captured two days ago are input to the predictor 22 and one prediction result is obtained. In this case, evaluation results for first cell images captured at multiple points of time are input even in a case where the predictor 22 performs the machine learning.

Although it has been described in the aforementioned embodiment that the evaluation result of the third cell image is input to the predictor 22, at least one culture condition may be input in addition to the evaluation result of the third cell image. As the culture condition, there are types and amounts of culture media, am environmental temperature and humidity in the culture, and the presence or absence of growth factors. In this case, the aforementioned culture condition is input to the predictor 22 even in a case where the predictor 22 performs the machine learning. For example, the user may set and input the culture condition by using the input device 40.

Figure 14:
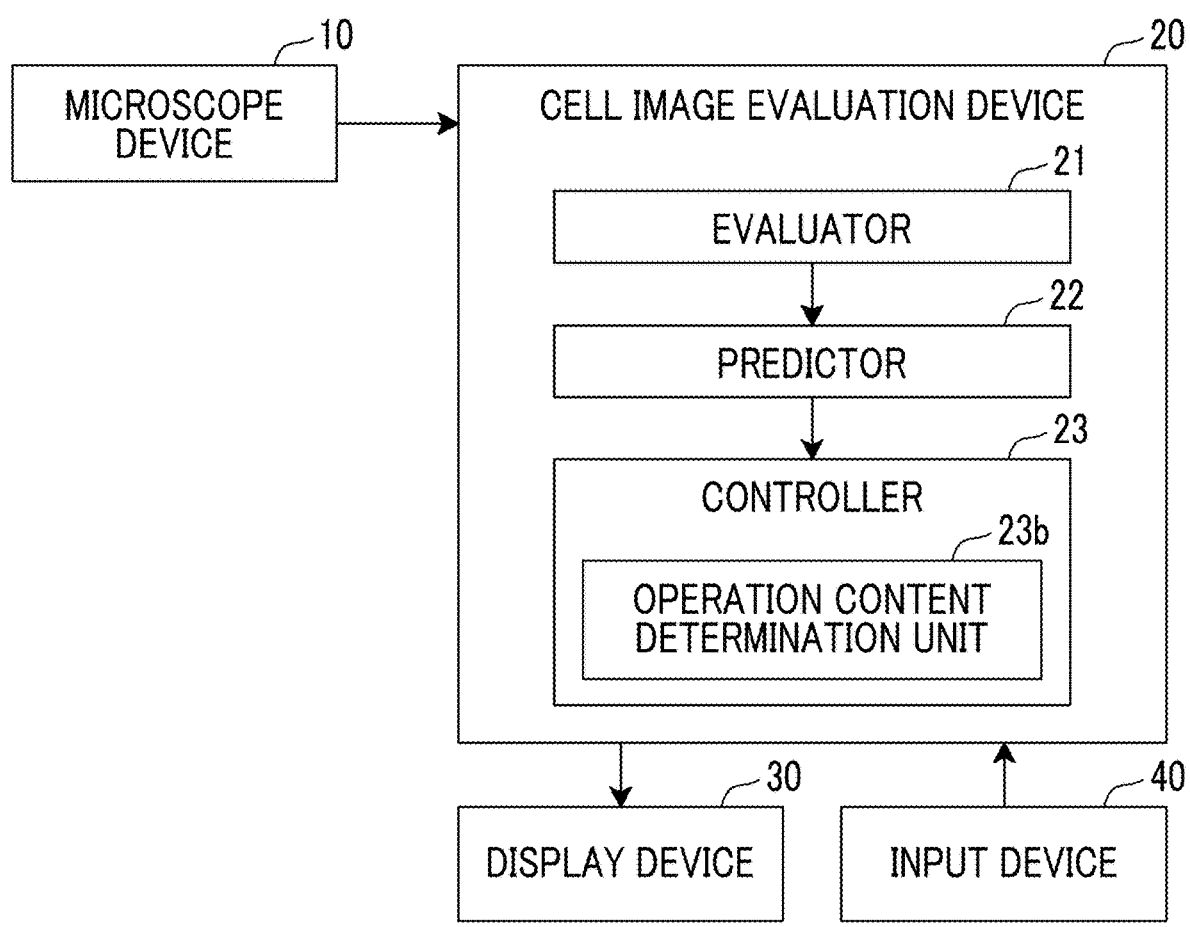
FIG. 14 is a block diagram showing a schematic configuration of a cell image evaluation prediction system using still another embodiment of the cell image evaluation device according to the present invention.

In the aforementioned embodiment, an operation content determination unit 23b that obtains information on the staining state of the cell output from the predictor 22, and determines an operation content for the cell based on the information of the staining state of the cell may be provided as shown in FIG. 14. Specifically, in a case where the ratio of the region of each staining emission intensity within the well is calculated as stated above, the operation content determination unit 23b may determine an operation such as subculturing, culture medium replacement, culture medium change, agent addition, and picking based on the ratio of the region of each staining emission intensity. The operation content determined by the operation content determination unit 23b is displayed on the display device 30, and the user is urged to perform this operation.

The staining states are obtained for each well in this manner, and thus, it is possible to recognize a culture state for each well. Accordingly, it is possible to efficiently perform the operation such as subculturing, culture medium replacement, culture medium change, agent addition, and picking. In a case where the staining states are obtained for each colony, it is possible to recognize a culture state for each colony. Accordingly, it is possible to efficiently perform the operation such as subculturing, culture medium replacement, culture medium change, agent addition, and picking. Particularly, in a case where picking is performed for each colony, it is possible to efficiently select the colony.

The operation content determined by the operation content determination unit 23b is not limited to the aforementioned example, and the operation content may be displayed on the display device 30 so as to urge the user to perform genetic testing. Specifically, for example, the quality of the cell may be evaluated based on the information on the staining state of the cell, and the user may be urged to perform the genetic testing in a case where the quality thereof is lower than a preset reference value and the quality is bad. In a case where a class of "unknown" may be set as the prediction result of the staining state of the cell, the user may be urged to perform the genetic testing in a case where the number of times this class appears is large, and thus, the staining state of the cell may be confirmed.

Although it has been described in the aforementioned embodiment that the evaluator 21 evaluates whether the cells are the undifferentiated cells or the differentiated cells, the present invention is not limited thereto. For example, the evaluator 21 may evaluate whether the cells within the region of interest are fibroblasts or feeder cells. The fibroblasts are one of cells constituting skin. The evaluator 21 evaluates whether the cell is the fibroblast or the feeder cell, and the predictor 22 performs the machine learning of the staining state of the fibroblast. Accordingly, it is possible to predict the staining state of the fibroblast.

The evaluator 21 may evaluate whether the cells within the region of interest are pluripotent stem cells or feeder cells. As the pluripotent stem cell, there are iPS cells and ES cells. The evaluator 21 evaluates whether the cell is the pluripotent stem cell or the feeder cell, and the predictor 22 performs the machine learning of the staining state of the pluripotent stem cell. Accordingly, it is possible to predict the staining state of the pluripotent stem cell.

The evaluator 21 may evaluate whether the region of interest is a cell region or a non-cell region.

The evaluator 21 may evaluate whether the cells within the region of interest is living cells or dead cells. As the method of evaluating whether the cells are the living cells or the dead cells, for example, the nucleoli included in the cell may be extracted, the cell including the nucleoli may be evaluated as the living cell, and the cell without including the nucleolus may be evaluated as the dead cell.

EXPLANATION OF REFERENCES

10: microscope device
20: cell image evaluation device
21: evaluator
22: predictor
23: controller
23a: integration unit
23b: operation content determination unit
30: display device
40: input device
CR: cell colony region
ER11: region
ER12: region
ER21: region
ER22: region
ER31: region
ER32: region
R: region of interest
SR: specific region of interest
W: well

What is claimed is:

1. A cell image evaluation device comprising:
an evaluator that evaluates states of cells included in each region of interest for each region of interest of a cell image obtained by imaging cells, and outputs evaluation results; and
a predictor that performs, in advance, machine learning of a relationship between evaluation results of the evaluator for regions around a specific region of interest within at least one first cell image obtained by imaging cells before a staining process and staining states of cells of the specific region of interest within a second cell image obtained by imaging the same imaging targets as the cells of the first cell image after the staining process,
wherein the predictor predicts staining states of cells of a specific region of interest based on evaluation results for regions around the specific region of interest among the evaluation results of the evaluator for at least one third cell image obtained by imaging cells before the staining process, and outputs the predicted staining states.

2. The cell image evaluation device according to claim 1, wherein the predictor outputs transition probabilities of two or more staining color intensities, as outputs of the staining states of the cells.

3. The cell image evaluation device according to claim 2, wherein the predictor receives, as inputs, the evaluation results for the third cell image obtained by imaging an inside of a container that contains cells, and outputs staining states of cells of a plurality of regions of interest within the container, and
the cell image evaluation device further comprises an integration unit that integrates the staining states of the cells of each region of interest, and obtains staining states of the cells of the entire container.

4. The cell image evaluation device according to claim 2, wherein the predictor receives, as an input, at least one culture condition.

5. The cell image evaluation device according to claim 3, wherein the predictor outputs the transition probabilities of the two or more staining color intensities, as the outputs of the staining states of the cells, and
the integration unit integrates the transition probabilities of the two or more staining color intensities of each region of interest for each staining color intensity, and obtains the staining states of the cells of the entire container.

6. The cell image evaluation device according to claim 3, wherein the predictor outputs the transition probabilities of the two or more staining color intensities, as the outputs of the staining states of the cells, and
the integration unit integrates the staining color intensities of the highest transition probabilities of the transition probabilities of the two or more staining color intensities of each region of interest, and obtains the staining states of the cells of the entire container.

7. The cell image evaluation device according to claim 1, wherein the predictor receives, as inputs, the evaluation results for the third cell image obtained by imaging an inside of a container that contains cells, and outputs staining states of cells of a plurality of regions of interest within the container, and
the cell image evaluation device further comprises an integration unit that integrates the staining states of the cells of each region of interest, and obtains staining states of the cells of the entire container.

8. The cell image evaluation device according to claim 7, wherein the predictor outputs the transition probabilities of the two or more staining color intensities, as the outputs of the staining states of the cells, and
the integration unit integrates the transition probabilities of the two or more staining color intensities of each region of interest for each staining color intensity, and obtains the staining states of the cells of the entire container.

9. The cell image evaluation device according to claim 7, wherein the predictor outputs the transition probabilities of the two or more staining color intensities, as the outputs of the staining states of the cells, and
the integration unit integrates the staining color intensities of the highest transition probabilities of the transition probabilities of the two or more staining color intensities of each region of interest, and obtains the staining states of the cells of the entire container.

10. The cell image evaluation device according to claim 1,
wherein the predictor receives, as an input, at least one culture condition.

11. The cell image evaluation device according to claim 1,
wherein the evaluator evaluates at least whether the cells are in an undifferentiated state or a differentiated state.

12. The cell image evaluation device according to claim 1,
wherein the evaluator evaluates at least a density of nucleoli.

13. The cell image evaluation device according to claim 1,
wherein the evaluator evaluates at least a density of white streaks.

14. The cell image evaluation device according to claim 1,
wherein the evaluator evaluates at least whether the cells are fibroblasts or feeder cells.

15. The cell image evaluation device according to claim 1,
wherein the evaluator evaluates at least whether the cells are pluripotent stem cells or feeder cells.

16. The cell image evaluation device according to claim 1,
wherein the evaluator evaluates at least whether the cells are cells or non-cells.

17. The cell image evaluation device according to claim 1,
wherein the evaluator evaluates at least whether the cells are living cells or dead cells.

18. The cell image evaluation device according to claim 1, further comprising:
an operation content determination unit that obtains information on the staining state of the cell output from the predictor, and determines an operation content for the cell based on the information on the staining state of the cell.

19. The cell image evaluation device according to claim 18,
wherein the operation content for the cell is subculturing, culture medium replacement, culture medium change, agent addition, picking, or genetic testing.

20. A non-transitory computer readable recording medium storing a cell image evaluation program causing a computer to function as:

an evaluator that evaluates states of cells included in each region of interest for each region of interest of a cell image obtained by imaging cells, and outputs evaluation results; and a predictor that performs, in advance, machine learning of a relationship between evaluation results of the evaluator for regions around a specific region of interest within at least one first cell image obtained by imaging cells before a staining process and staining states of cells of the specific region of interest within a second cell image obtained by imaging the same imaging targets as the cells of the first cell image after the staining process, wherein the predictor predicts staining states of cells of a specific region of interest based on evaluation results for regions around the specific region of interest among the evaluation results of the evaluator for at least one third cell image obtained by imaging cells before the staining process, and outputs the predicted staining states.

* * * * *